US010780262B2

(12) United States Patent
Brindley et al.

(10) Patent No.: US 10,780,262 B2
(45) Date of Patent: Sep. 22, 2020

(54) METHOD OF ASSEMBLING AN ELECTRODE ARRAY THAT INCLUDES A PLASTICALLY DEFORMABLE CARRIER

(71) Applicant: Stryker Corporation, Kalamazoo, MI (US)

(72) Inventors: Robert Brindley, Delton, MI (US); John Janik, Hudsonville, MI (US)

(73) Assignee: Stryker Corporation, Kalamazoo, MI (US)

( * ) Notice: Subject to any disclaimer, the term of this patent is extended or adjusted under 35 U.S.C. 154(b) by 1152 days.

(21) Appl. No.: 14/829,200

(22) Filed: Aug. 18, 2015

(65) Prior Publication Data

US 2015/0352350 A1    Dec. 10, 2015

Related U.S. Application Data

(62) Division of application No. 12/475,920, filed on Jun. 1, 2009, now abandoned.

(60) Provisional application No. 61/057,684, filed on May 30, 2008.

(51) Int. Cl.
*A61N 1/05* (2006.01)
*C23C 14/00* (2006.01)

(52) U.S. Cl.
CPC ............ *A61N 1/05* (2013.01); *C23C 14/0005* (2013.01); *A61B 2562/125* (2013.01); *A61N 1/0529* (2013.01); *A61N 1/0541* (2013.01); *A61N 1/0543* (2013.01); *A61N 1/0551* (2013.01); *Y10T 29/49124* (2015.01)

(58) Field of Classification Search
CPC ...... A61N 1/05; A61N 1/0529; A61N 1/0541; A61N 1/0543; A61N 1/0551
See application file for complete search history.

(56) References Cited

U.S. PATENT DOCUMENTS

| 4,969,468 | A | 11/1990 | Byers et al. |
| 6,066,512 | A | 5/2000 | Hashimoto |
| 6,324,429 | B1 | 11/2001 | Shire et al. |
| 6,415,187 | B1 | 7/2002 | Kuzma et al. |
| 2002/0198573 | A1* | 12/2002 | Nisch ............ A61F 2/14 607/54 |
| 2004/0186543 | A1 | 9/2004 | King et al. |

(Continued)

FOREIGN PATENT DOCUMENTS

| KR | 2003/035738 A | 5/2003 |
| KR | 20030035738 A * | 5/2003 |

(Continued)

OTHER PUBLICATIONS

European Patent Office, "International Search Report and Written Opinion" for PCT/US2009/045602, dated Nov. 10, 2009.

*Primary Examiner* — Livius R. Cazan
(74) *Attorney, Agent, or Firm* — Howard & Howard Attorneys PLLC

(57) ABSTRACT

A method of assembling an implantable electrode array from a coupon (108) formed from plastically deformable material. Layers of material are disposed on the coupon to form the electrodes (48) and conductors (62) of one or more electrode arrays. Sections of the coupon on which the electrodes and conductors are removed, along with the electrodes and conductors to form the electrode arrays. The removed sections of the coupon thus function as plastically deformable carriers (74) for the arrays (40).

22 Claims, 18 Drawing Sheets

(56) References Cited

U.S. PATENT DOCUMENTS

| | | | |
|---|---|---|---|
| 2005/0032223 A1 | 4/2005 | Yoon | |
| 2007/0123766 A1 | 5/2007 | Whalen, III et al. | |
| 2008/0046050 A1 | 2/2008 | Skubitz et al. | |
| 2009/0033769 A1 | 2/2009 | Nagaoka et al. | |
| 2010/0330748 A1* | 12/2010 | Chu | H01L 51/0024 438/127 |
| 2010/0331935 A1 | 12/2010 | Tabada et al. | |

FOREIGN PATENT DOCUMENTS

| | | |
|---|---|---|
| WO | 2001/83026 A1 | 11/2001 |
| WO | 2002/089907 A1 | 11/2002 |
| WO | 2007/084540 A3 | 7/2007 |
| WO | 2008/080073 A3 | 7/2008 |
| WO | 2009/111142 A2 | 9/2009 |

\* cited by examiner

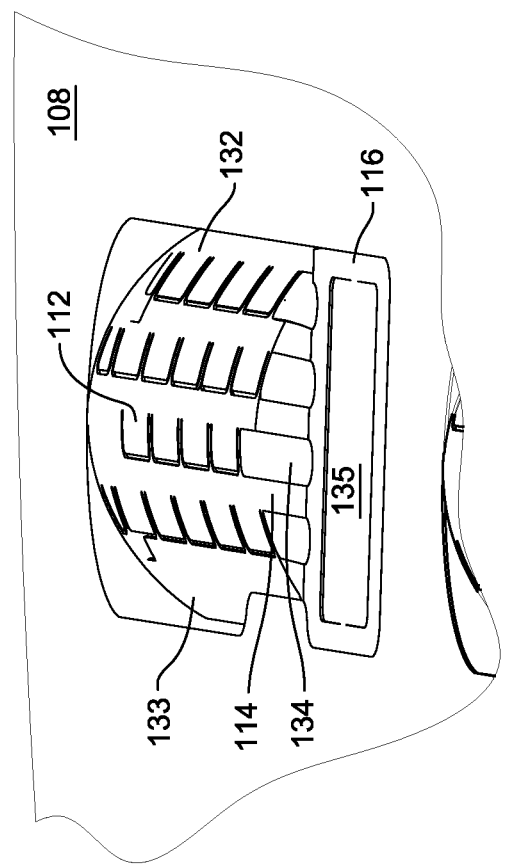

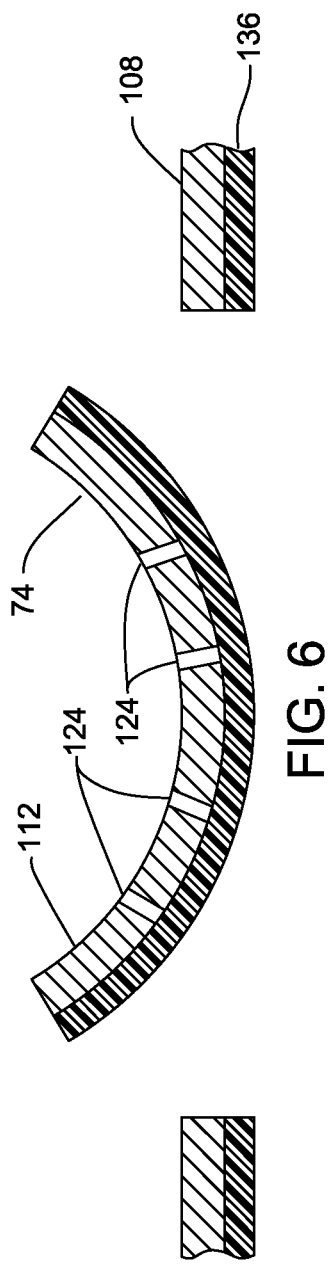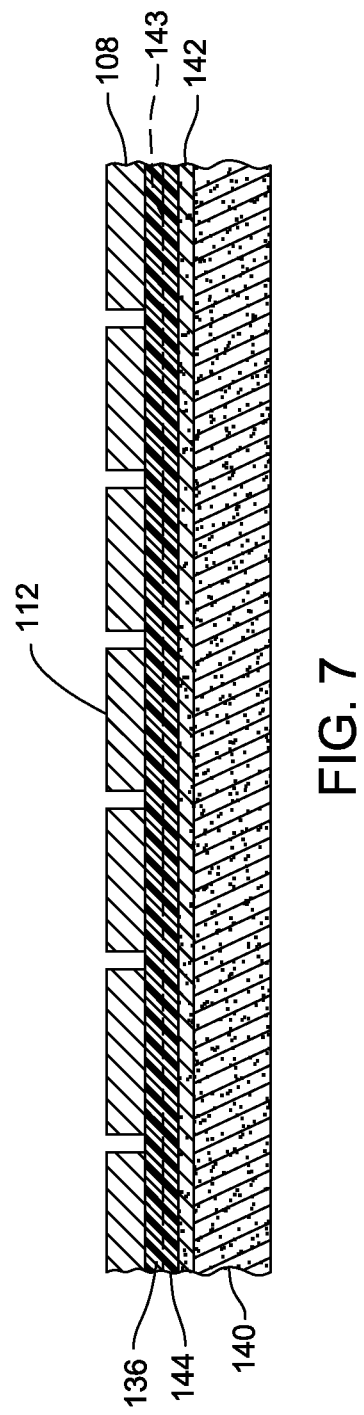
FIG. 6
FIG. 7

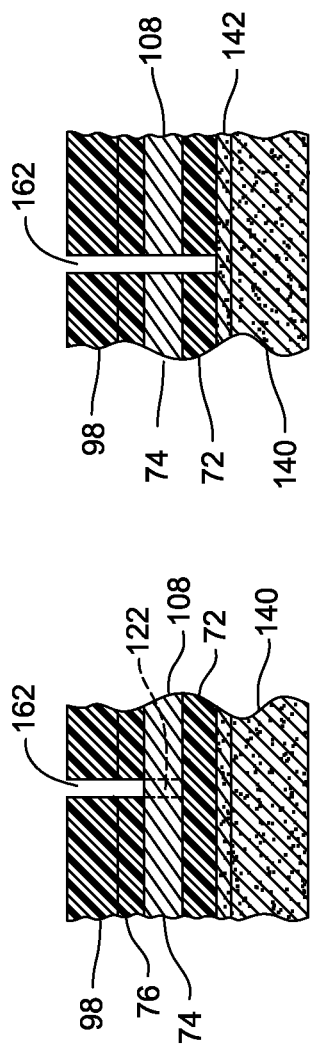
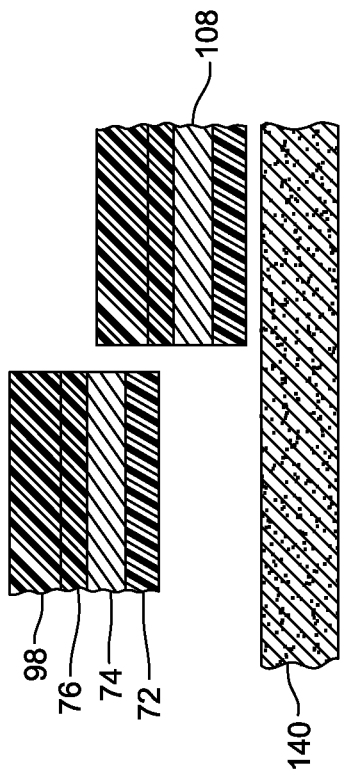
FIG. 13
FIG. 14
FIG. 15

METHOD OF ASSEMBLING AN ELECTRODE ARRAY THAT INCLUDES A PLASTICALLY DEFORMABLE CARRIER

RELATIONSHIP TO EARLIER FILED APPLICATION

This application is a divisional of U.S. patent application Ser. No. 12/475,920 filed 1 Jun. 2009, now abandoned. Application Ser. No. 12/475,920 is a claims priority from and is nonprovisional of U.S. Patent Application No. 61/057,684 filed 30 May 2008. The above-identified priority applications are now incorporated herein by reference.

FIELD OF THE INVENTION

This invention is generally related to a method of assembling electrodes arrays that include plastically deformable carriers. More particularly, this application is directed to a method that facilitates the batch, simultaneous assembly of plural electrode arrays.

BACKGROUND OF THE INVENTION

A number of medical procedures involve implanting an electrode array in a patient to accomplish a desired therapeutic effect. Generally, the electrode array includes a non-conductive carrier on which typically two or more electrodes are disposed. Once the electrode array is implanted, current is flowed from at least one of the electrodes, through the adjacent tissue, to at least one of the other electrodes. The current flow through the tissue stimulates the tissue to accomplish a desired therapeutic result. For example, an electrode array positioned adjacent the heart may flow currents to stimulate the appropriate contraction and expansion of the heart muscles. There is an increasing interest in implanting electrode arrays adjacent neurological tissue so that the resultant current flow stimulates a desired neurological effect. Thus, the current flowed between the electrodes of such an array can be used to reduce the sensation of chronic pain perceived by the brain. Alternatively, the current flow stimulates a feeling of satiation as part of an appetite suppression/weight management therapy. In another application, the current is flowed to muscles associated with the bladder or the anal sphincter to assist in control of incontinence.

Implicit for the above therapies to work, the current must flow through very small sections of tissue through which such flow will cause the desired result. Likewise, the current should not be flowed through adjacent tissue if such flow would result in undesirable side effects. Even if the flow of the current through some tissue does not result in undesirable side effects, such current flow is a needless sink of power. Accordingly, for an implanted electrode array to provide the greatest benefit, it is necessary that the electrodes be positioned as closely as possible adjacent the tissue through which the current is to be flowed.

One means to accomplish the goal of precisely targeted current flow is to provide the electrode array with a matrix, rows and columns, of spaced apart electrodes. The array is implanted over a relatively large section of tissue that includes the tissue through which the current flow will offer the desired therapeutic effect. Once the array is implanted, the current is flowed between different combinations of electrodes. As a result of the current flowing between different electrodes, the current flows through different sections of the underlying tissue. The response of the patient to the current flow through the different sections of tissue is monitored to determine through which section of tissue the current flow has the most beneficial effects and/or most tolerable side effects. This type of electrode assembly thus provides relatively precise targeting of current flow through tissue so that such flow has the greatest potential for positive results and minimal adverse effects.

For the above electrode array assembly to potentially be of benefit, the assembly should occupy a relatively large surface area. The above type of assembly are for example known to have a width of 0.25 cm or more and a length of 0.5 cm or larger. To position this type of electrode array assembly against target tissue, it is suggested that a surgical procedure is required in which an incision is cut in the patient to access the surface of the tissue over which the assembly is to be positioned. The assembly is then fitted over the tissue and the incision cut in the overlying tissue is closed.

An electrode array assembly designed to eliminate having to expose a patient to the above surgical trauma is disclosed by the Applicants' Patent Application FOLDABLE, IMPLANTABLE ELECTRODE ARRAY ASSEMBLY AND TOOL FOR IMPLANTING SAME, U.S. Pat. App. No. 61/034,367, filed 6 Mar. 2008, the contents of which are published in PCT Pat. App. No. PCT/US2009/033769, PCT. Pub. No. WO 2009/111142 and U.S. Pat. Pub. No. 2011/0077660 A1, and which is explicitly incorporated herein by reference. The electrode array assembly of this invention includes a carrier formed from superelastic material. A superelastic material is a material that though rigid, will, after being subjected to relatively high degree of bending or folding, substantially return to its initial shape. The superelastic material forming the carrier of the disclosed electrode assembly is a nickel titanium alloy. Another feature of using the nickel titanium alloy as the carrier is that this material is plastically deformable, the carrier can be formed into a particular shape without fracturing. Other components of the electrode array assembly, the electrodes and the conductors that extend to the electrodes, are disposed on the carrier.

Since the carrier is formed from a shape memory material, the electrode array assembly can be folded or rolled into a delivery cannula that has a width appreciably less than the width of the assembly itself. Thus, an electrode assembly having a width of 12 mm can be rolled or folded to fit in a delivery cannula having a major diameter of 6 mm or smaller. This means that one can implant the electrode assembly of this invention, by forming a relatively small portal in the body that is directed to the site at which the assembly is to be implanted. The delivery cannula, with the electrode assembly contained therein, is inserted in the portal and directed to the target site. The electrode assembly is then discharged, deployed, from the cannula. Upon deployment, owing to the presence of the superelastic carrier, the electrode assembly, when disposed over the tissue, unfolds or unrolls to its initial shape. Current is then flowed between different sets of electrodes to determine which current flow has the most beneficial and/or less adverse effect.

An advantage of the above electrode array assembly is that it only requires the formation of a relatively small opening in the patient to be properly positioned. The trauma and side effects associated with surgical procedures in which larger openings are created are eliminated.

For the above electrode array assembly to have appreciable therapeutic utility, it is desirable to have means that makes it possible to efficiently fabricate the assembly.

SUMMARY OF THE INVENTION

This invention relates generally to a method for assembling an electrode array assembly that includes a carrier formed from superelastic material. The method of this invention facilitates the simultaneous, batch fabrication of plural electrode array assemblies.

One aspect of the method of this invention is that the conductive components forming an electrode array assembly are fabricated over or otherwise bonded to a layer of material that eventually functions as the superelastic carrier.

Another aspect of the method of this invention is that, during the fabrication process, a backing is disposed below the superelastic carrier. The backing provides rigidity to the carrier so the carrier can withstand the forces of the processes in which the conductive components are fabricated over or otherwise bonded to the carrier.

Another aspect of the method of this invention is that the method makes it possible to in a single set of fabrication sub-steps, simultaneously assembly plural electrode array assemblies.

A further aspect of this invention is the method makes it possible to, using two-dimensional fabrication techniques, form an electrode array assembly on a carrier that already has features in three dimensions; length, width and height in/out of a reference plane.

BRIEF DESCRIPTION OF THE DRAWINGS

The invention is pointed out with particularity in the claims. The above and further features and advantages of this invention are understood by reference to the following Detailed Description in conjunction with the accompanying drawings in which:

FIG. 5A is a perspective view of an individual carrier of FIG. 5;

FIG. 6 is a cross sectional view of a section of the sheet of superelastic material showing the coating on the sheet and one of the carriers on the sheet;

FIG. 7 is a cross sectional view of the section of the sheet of superelastic material bound to a support wafer;

FIG. 13 is a cross sectional view of the essentially fabricated electrode array assembly showing one of the sheet-to-carrier retaining tabs immediately prior to the removal of the tab;

FIG. 14 is a cross sectional view of the section of the sheet of superelastic material of FIG. 13 illustrating the separation between the electrode array assembly and the sheet after removal of the tab and underlying parylene-C layer;

FIG. 15 is a cross sectional view of the section of the electrode array assembly and surrounding sheet of FIG. 14 illustrating lift off of the assembly after removal of the sacrificial layer;

DETAILED DESCRIPTION

I. Electrode Array Assembly

Figure 1:
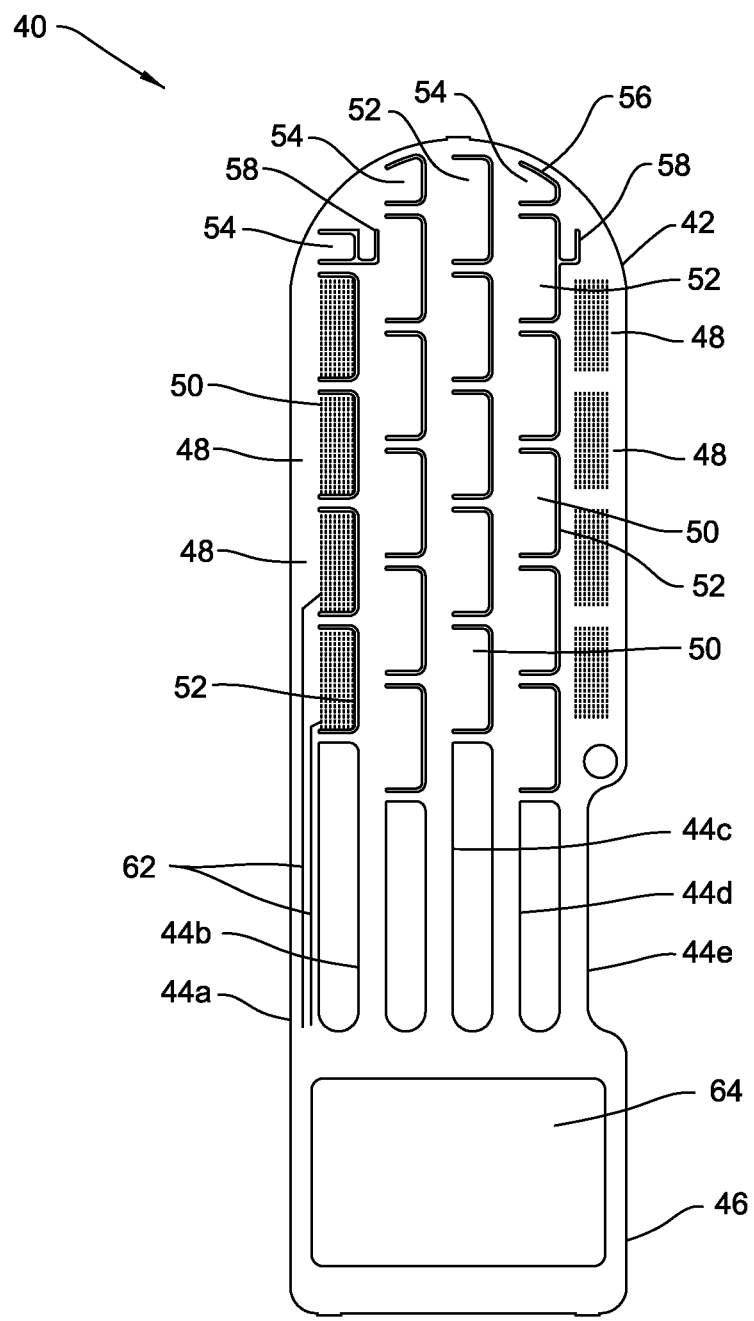
FIG. 1 is a plan view of an electrode assembly constructed in accordance with this invention wherein certain normally covered components are shown exposed for purposes of illustration.

FIG. 1 is a plan view of an electrode array assembly 40 fabricated according to the method of this invention. Assembly 40 includes a head 42. Spaced from the head 42 is a foot 46. A number of parallel, spaced apart legs 44a-e extend rearward from the distal end of the head 42 to connect the foot 46 to the head. A number of columns of spaced-apart electrodes 48 are disposed on assembly head 42. Each column of electrodes includes a number of longitudinally spaced apart electrodes 48. For ease of illustration, in FIG. 1, only the first and fifth columns of electrodes 48 are shown; only two electrodes in each column are identified. Each electrode 48 in the first four (4) columns of electrodes, when viewed from the left side to the right side of the drawing, is disposed on a tab 50 formed in the head 42. Each tab 50 is defined by a three sided-slot 52 that extends through the head 42. In the illustrated version of the invention, an auxiliary tab 54 is formed in the head forward of the proximal most electrode 48 in the first, second and fourth columns of electrodes. Each auxiliary tab 54 is defined by a slot 56 that extends through assembly head 42. Supplementary slots 58 extend from the first column auxiliary tab 54 and the forward most tab 52 of the fourth column of tabs 52.

A conductor 62 extends to each electrode 48. (For ease of illustration, only two conductors 62 are shown.) Each conductor 62 extends from the assembly head, over one of the legs 44a, 44b, 44c, 44d or 44e to assembly foot 46.

Foot 46 is formed to define a center opening 64. Center opening 46 is dimensioned to receive a cable assembly not illustrated and not part of this invention. The individual assembly conductors 62 are connected to conductors internal to the cable. The cable conductors supply current that is applied through conductors 62 to the electrodes 48 to cause current flow between the electrodes. U.S. Pat. App. No. 60/871,675 filed 22 Dec. 2006, refilled as PCT App. No. PCT/US2007/088580 and published, as PCT Pub. No. WO 2008/080073 A2 the contents of which are each hereby explicitly incorporated by reference, describes an alternative means to provide current to the electrodes 48. The assembly of this document discloses how components external to the electrode array assembly 40 supply both power for sourcing current through the electrodes 48 and instructions that indicate between which electrodes the current should be flowed. Signals that contain both the power and instructions are supplied to components mounted to the assembly foot 46, (components not illustrated and not part of this invention). In these constructions of the electrode array assembly 40, conductors 62 extend to these components. Again, it should be appreciated that the methods by which current is sourced to the electrodes 48 and the structural features on the assembly 40 that facilitate such current sourcing are not relevant to this invention.

Figure 2:
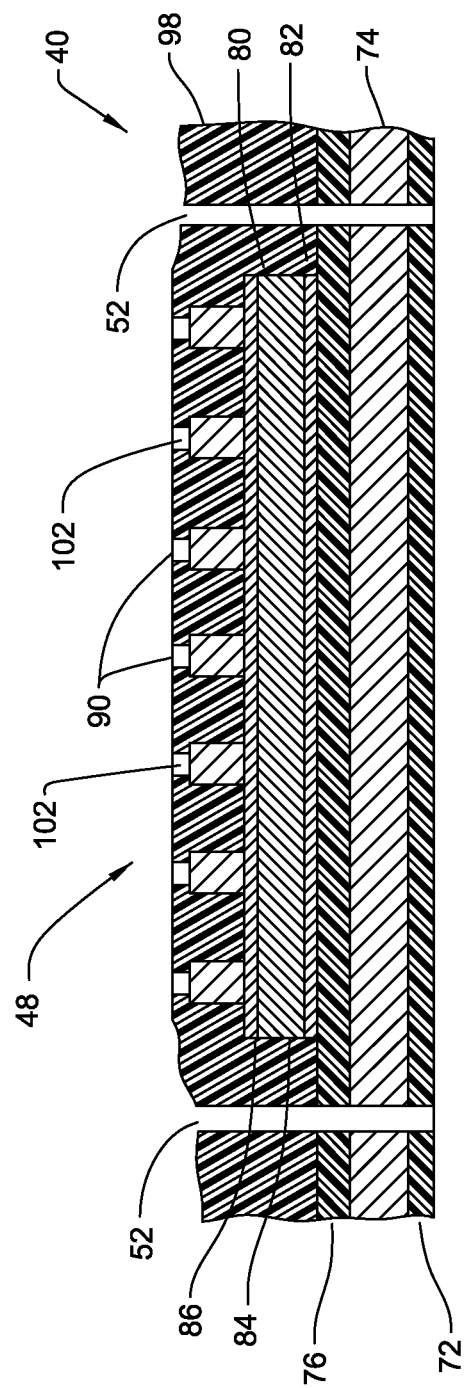
FIG. 2 is a cross sectional view of a single electrode of the electrode assembly of FIG. 1.

As seen best in FIG. 2, assembly 40 includes a carrier 74 formed from material that is plastically deformable and, in many versions of the invention, superelastic. For this assembly, the carrier is considered "plastically deformable" if the shape of the carrier can be altered by stressing, heat treatment or by chemical or metallurgical transformation to take on a formed shape without fracturing. The carrier is considered to be "superelastic" if, after being shaped, the carrier can be bent, folded or otherwise deflected and, upon being released from the stress of the forces applying this deflection, return to its formed shape. Carrier 74, as is all the components forming assembly 40, is formed from material that is biocompatible, that is material that, when implanted in living tissue, typically does not become a source of infection. In some versions of the invention carrier 74 is a layer of nitinol, a nickel titanium alloy. Carrier 74 has a thickness of 50 microns. Disposed below and around the sides of carrier 74 is a lower insulating layer 72 formed from electrically insulating material. In one version of the invention, insulating layer 72 is a polyxylene polymer film, such as parylene-C. Lower insulating layer 72 has a thickness of at least 1 micron. An upper insulating layer 76 is disposed on top of the carrier 74. Upper insulating layer 76 can be formed from the same material from which lower insulating layer 72 is formed. Upper insulating layer 76 has a thickness of at least 1 micron.

Electrodes 48 and conductors 62 are formed above the upper insulating layer 76. Each electrode 48 can have surface area as small as 50 microns$^2$ and, in some versions of the invention, as small as 10 microns$^2$. The minimal on-carrier separation between each electrode can be as small as 15 microns and in some versions of the invention, as small a distance as 5 microns.

Each electrode 48 includes a conductive base pad 80 from which a number of conductive buttons 90 project. Each base pad 80 includes a bottom layer 82, an intermediate layer 84 and a top layer 86. The base pad bottom and top layers 82 and 86, respectively, are formed from chrome. In some versions of the invention, electrode base pad bottom layer 82 and top layer 86 each have a thickness of at least 500 Angstroms. Bottom layer 82 and top layer 86 are provided because chrome bonds to both polyxylene polymer and gold. Gold is the material from which base pad intermediate layer 84 is formed. Often, intermediate layer 84 has a thickness of 5 microns or less. Intermediate layer 84, as discussed below, is also integral with the conductors 62. The various sections of intermediate layer 84 functions as the low resistance components of the electrodes 48 and the conductors 62.

Each conductive button 90 typically has a circular cross sectional profile in the lateral plane. The diameter of the button is typically is at least 10 microns. In many versions of the invention, the cross-sectional diameter of the button 90 is between and 20 and 30 microns. The minimal separation between adjacent buttons 90 is 0.5 microns. In some versions of the invention, the separation is 1.0 or more microns. In some versions of the invention, each button 90 is formed from iridium and has a thickness of at least 1000 Angstroms.

While not illustrated, it should be understood that each conductor 62 is formed from a chrome bottom layer, a gold intermediate layer and a chrome top layer. Conductors 62 are formed simultaneously with the electrode base pads 80. Accordingly, the conductor base layers are contiguous with and have the same thickness as the electrode base pad base layers 82. The conductor intermediate layers are contiguous with and have the same thickness as the electrode base pad intermediate layers 84. The conductor top layers are contiguous with and have the same thickness as the electrode base pad top layers 86.

An electrically non-conductive shell 98 is disposed over conductors 62 and the surfaces of the electrode base pads 80 that are button-free. Portions of the shell 98 also extend around the outer perimeters of the buttons 90. Openings 102 in the shell expose faces of the buttons 90 located inward from the outer perimeters of the buttons 90. Shell 98, like insulating layers 72 and 76, is formed from parylene-C polyxylene polymer film.

FIG. 2 is a cross sectional view along a line at least parallel to the longitudinal axis of a single one of the electrodes 48. Accordingly, also seen FIG. 2 are the parallel side sections of slot 52 that define the tab 50 (FIG. 1) on which the electrode 48 is seated.

Figure 1A:
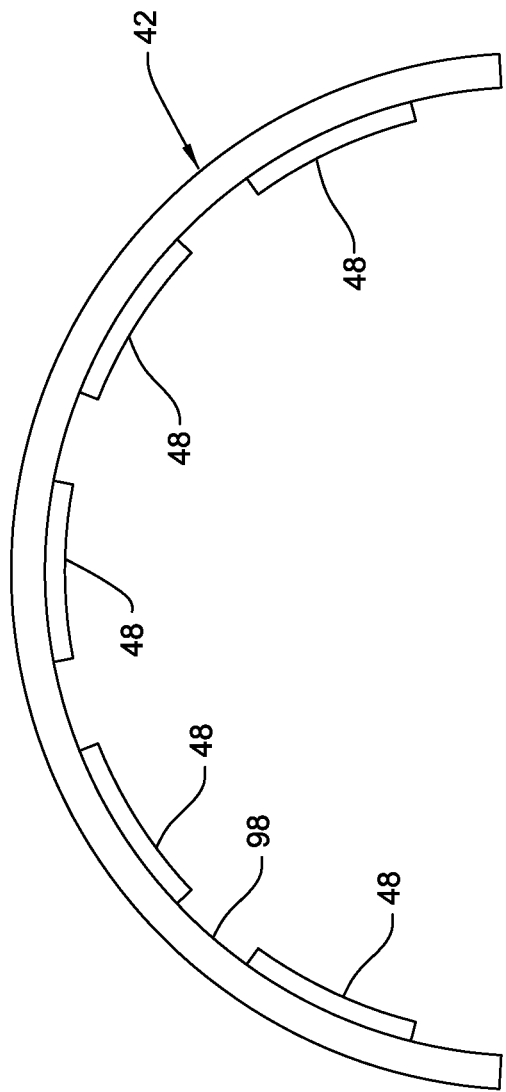
FIG. 1A is a front view of an electrode assembly of this invention depicting how the assembly may have an arcuate profile.

As represented by FIG. 1A, in some versions of the invention, at least head 42 of electrode array assembly 40 has an arcuate lateral cross section profile. Electrodes 48 are disposed on the inwardly curved surface of the carrier 74. In FIG. 1A, the extent to which electrodes 48 extend outward of the adjacent section of shell 98 is exaggerated for purposes of illustration. This embodiment of the invention is provided when assembly 40 is to be positioned over the surface of a section of tissue that itself is curved. The curvature of assembly 40 thus minimizes the gap between the electrodes 48 and the underlying tissue. The minimization of this gap reduces the loss of current flow between the electrodes and the tissue. For example, an electrode array assembly intended to be placed over the spinal dura may be provided with the above-described profile.

II. Method of Assembly

A process to manufacture electrode array assembly 40 using a method of this invention can start with the formation of the carrier. As seen by reference to FIG. 3 a sheet of the superelastic material, referred to as a coupon 108, is shaped to define at least one if not a plurality of carriers 74.

Figure 4A:
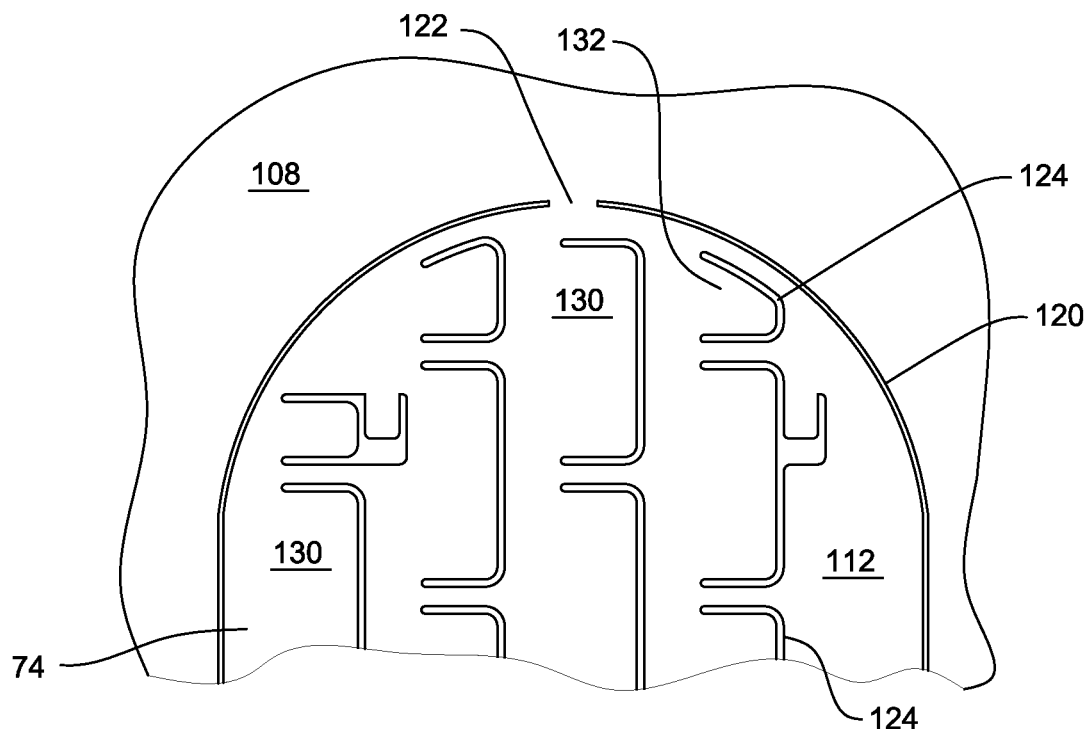
FIG. 4A is a plan view of an enlarged section of the coupon of superelastic material showing how the proximal front end of the carrier is retained to the sheet.
Figure 4B:
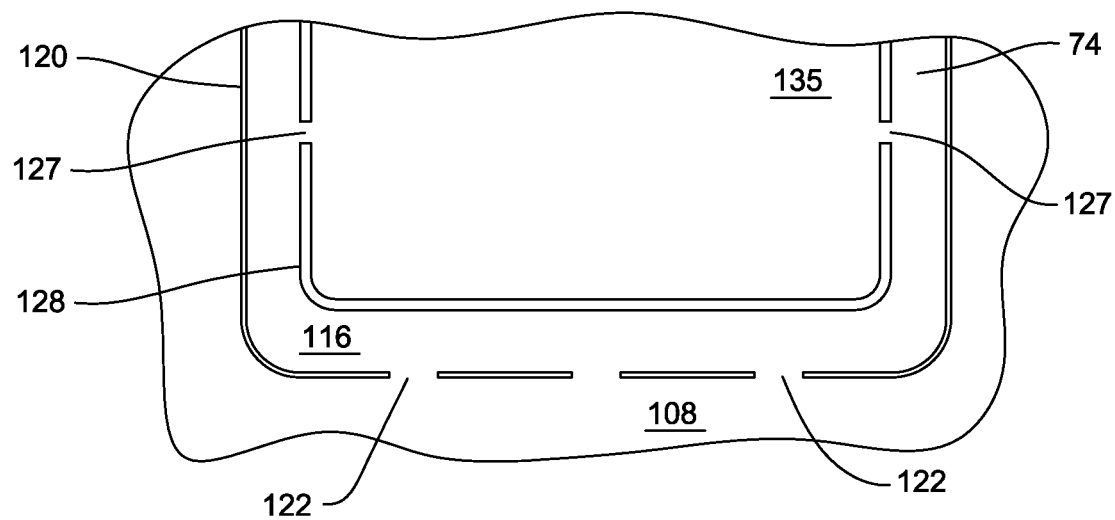
FIG. 4B is a plan view of an enlarged sections of the sheet of superelastic material showing how the distal rear end of the carrier is retained to the coupon.
Figure 4C:
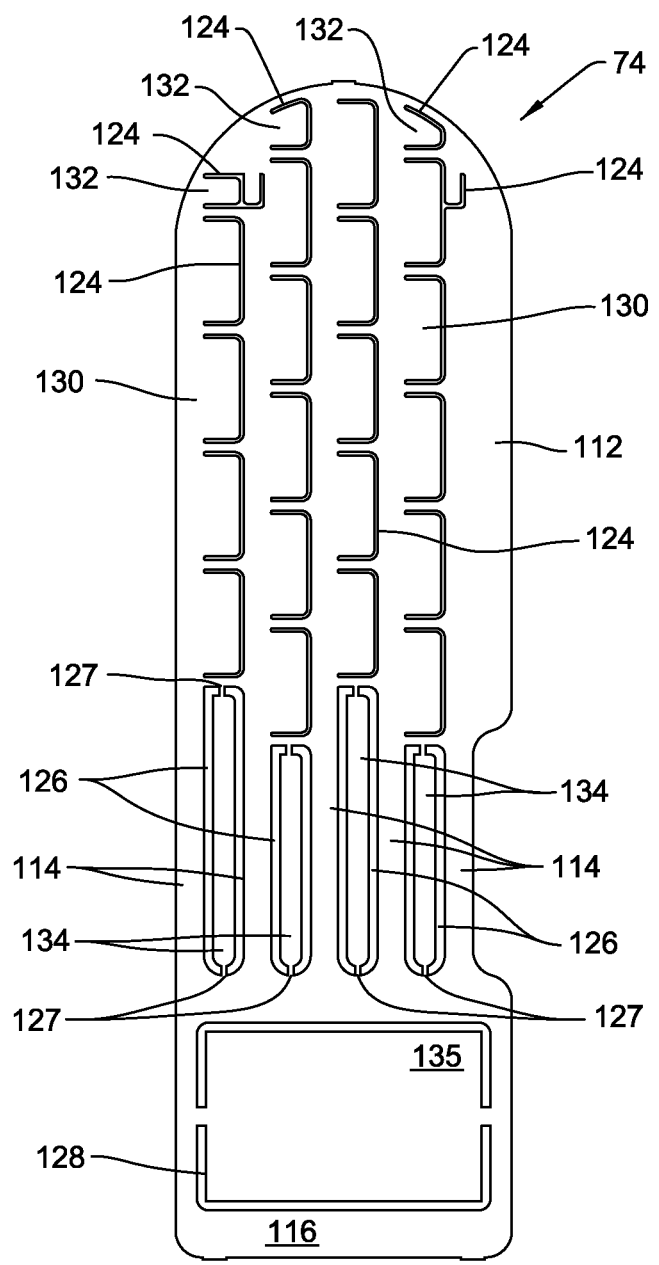
FIG. 4C is a plan view of a single carrier wherein the slits that define the waste slugs that are eventually separated from the carrier are shown.

According to the present invention, using a photo etch process or other processes, the coupon 108 is formed with a number of through openings that define both the perimeters of the individual carriers 74 and the features of each carrier. The perimeter, the outer shape of an individual carrier 74, is defined by a slot 120, seen in FIGS. 4A and 4B in the coupon 108. In this step, slot 120 is not formed so as to completely sever the carrier 74 from the surrounding section of the coupon 108. Instead, slot 120 is broken into sections by a number of retaining tabs 122 that extend between the carrier and the surrounding section of the coupon (individual slot sections not identified). As seen by FIG. 4A, a first retaining tab 122 extends between the most proximal end of the carrier head 112 and the rest of the coupon 108. From FIG. 4B, it can be seen that second and third spaced apart retaining tabs 122 extend from the distal end of foot 116 to the adjacent section of coupon 108.

In the process in which the perimeter of the carrier 74 is formed, the carrier 74 is further formed in this process to define a head 112, legs 114 and a foot 116. Carrier head 112, legs 114 and foot 116 become portions of, respectively, the assembly head 42, legs 44 and foot 46.

Formed simultaneously with slot 120 are slots 124, 126 and 128. Each one of the slots 124, 126 and 128 is formed wholly within the portion of the coupon that is a carrier 74. Each slot 124 defines one of the tabs 130 or 132 on the carrier 74. As is apparent in the following description, each carrier tab 130 becomes one of the electrode assembly tabs 50. Each carrier tab 132 becomes one of the electrode assembly auxiliary tabs 54. Slots 124 also define the carrier portions of the assembly auxiliary slots 58.

Each slot 126 defines what becomes a void space between adjacent legs 114 of the carrier. For purposes of later identification, each section of superelastic material defined by one of the slots 126 can be considered a slug 134. Slot 128 defines what becomes a rectangular opening in the carrier foot 116. For purposes of later identification, the rectangular section of superelastic material defined by slot 128 is identified as slug 135. Slots 126 and 128, like slot 120 are not closed loop slots. Instead, retaining tabs 127 break up each slot 126 and 128 into at least two if not more sub slots (individual sub-slots not identified).

Slots 120, 124, 126 and 128 are all typically no more than 4 microns wide. In some preferred methods of manufacture, slots 120, 124, 126 and 128 are 2 microns wide or smaller in width. The small widths of slots 120, 124, 126, and 128 substantially eliminates the instances of, during the subsequent fabrication processes, photo resists and other coatings developing a relatively thick bead on the surface of the carrier immediately behind the perimeter of the slot. Such beads can develop as a result of surface tension if the slots are relatively wide across.

Figure 3:
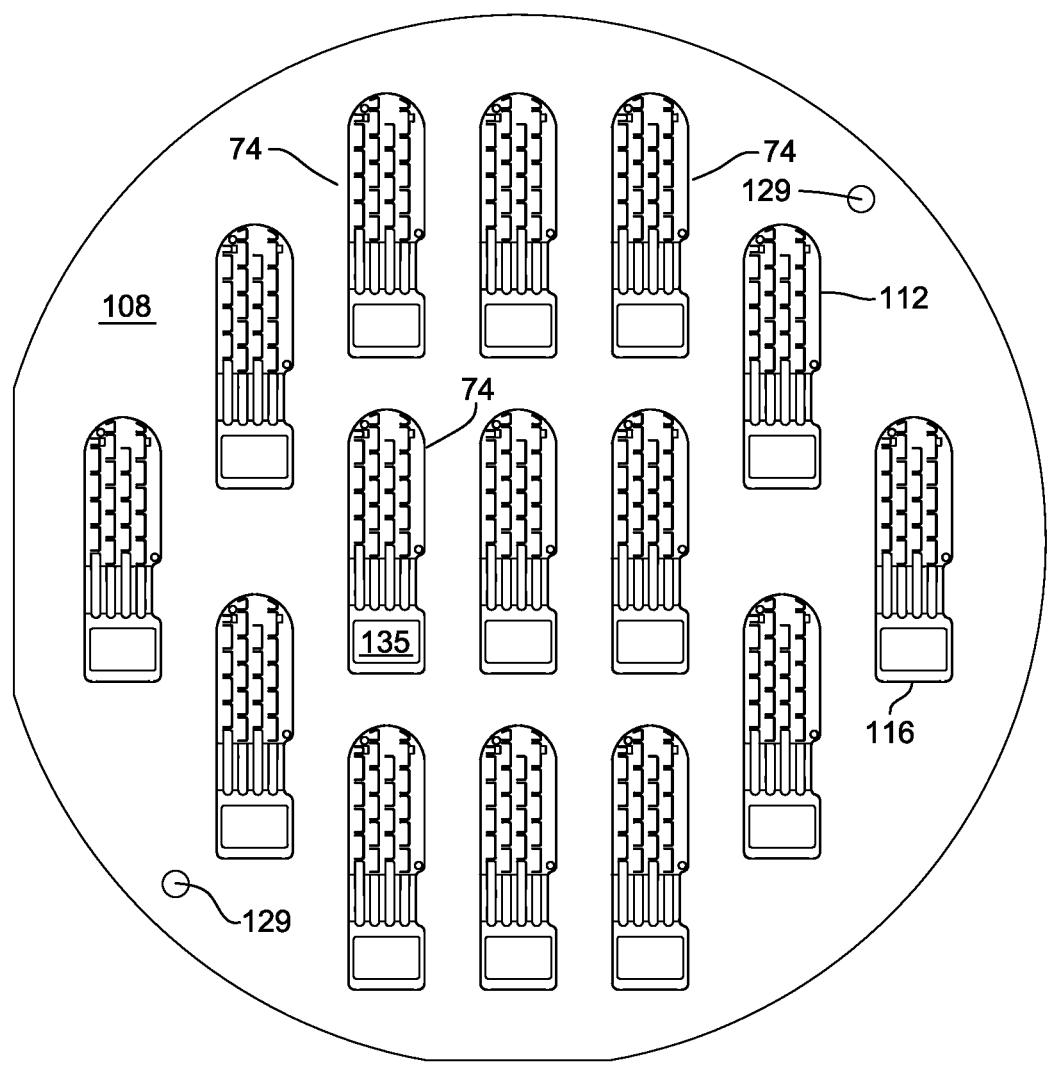
FIG. 3 is a plan view of a sheet, a coupon, of superelastic material on which plural carriers are formed.

Simultaneously with the forming of the individual carriers 74 and their feature-defining slots, alignment features are also formed in the coupon 108. In FIG. 3, openings 129 in carrier free sections of the coupon serve as the alignment features. This shaping of coupon 108 may be performed simultaneously with the process in which slots 120, 124, 126 and 128 are formed. In many method of assembly of this invention, the alignment features are slots formed in the sections of the coupon that do not function as carriers. The alignment features facilitate the precise overly of masks over the coupon 108 so that the subsequent layers of material are accurately laid down.

Figure 5:
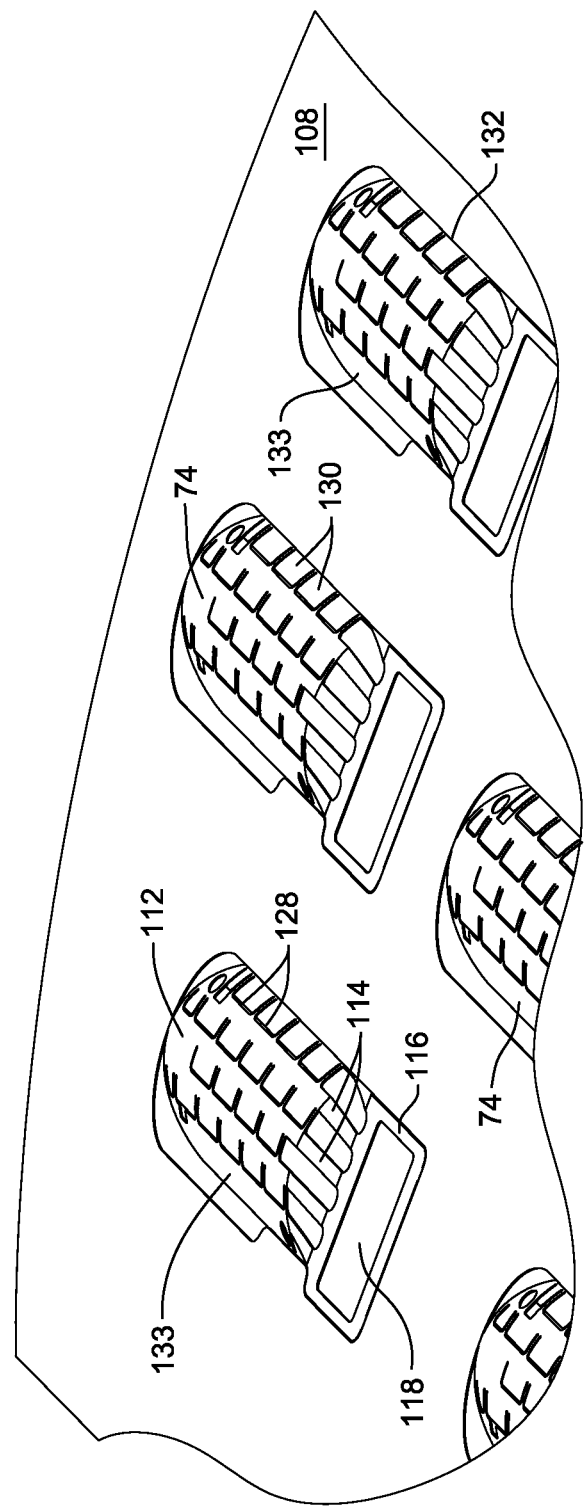
FIG. 5 is a perspective view illustrating how, while retained to the sheet of superelastic material, the individual carriers are curved.

Once slots 120, 124, 126 and 128 and the alignment features are formed in coupon 108, the carriers 74 are shape formed so that at least the heads 112 have the desired concavo-convex profile as seen in FIG. 5. This step may be performed by pressing the individual carriers between opposed dies that are appropriately shaped. Once the carriers are so pressed, heat is applied to set the carriers. The heat may be sourced from heaters in the individual dies, external heaters or heat transferred from liquid surrounding the dies. As a consequence of the simultaneous bending and heating of the carriers, the carriers develop the desired curved shape, undergo the desired plastic deformation. As seen in the detailed view of FIG. 5A, as a consequence of this process, the head 112 of each carrier 74 essentially has a pair of opposed wings 133. Each wing 133 extends along the side of the head 112 and curves away from the plane of the coupon 108.

As represented by FIG. 6, the underside of coupon 108, including the suspended carriers 74, is provided with a parylene-C coating 136. Here the "underside" of the sheet is understood to be the surface of sheet where in the carrier heads 112 have their convex profile. The parylene-C is deposited on the coupon 108 and carriers using a vapor deposition process. Parylene-C polymer is a conformal coating. Therefore, the even thought the carrier heads 112 have curved wings 133, the parylene-C still covers these portions of the carriers 74a. Parylene-C coating 136 has a thickness of at least 1 micron.

During the above process step it should be appreciated that slugs 134 and 135 remain attached to the individual carriers 74. Accordingly, whenever a material such as parylene is coated over the whole of a carrier 74, the material is also coated over slugs 134 and slug 135.

Coupon 108, with the carrier 74 still attached, is then bonded to a silicon wafer 140. Prior to this step, it should be appreciated that the silicon wafer 140 is prepared for this bonding process. This preparation includes initially forming a layer of silicon oxide 142 over silicon wafer 140. Silicon oxide layer 142 has a thickness of at least 1 micron. As will be apparent below, silicon oxide layer 142 functions as a sacrificial layer for the assembly process.

A layer 144 of parylene-C having a thickness of 1 micron is then formed over silicon oxide layer 142. Parylene-C layer 144 is formed over silicon oxide layer 142 by a vapor deposition process.

Once the parylene-C layer 144 is formed over layer 142, coupon 108 is ready for bonding to wafer 140. Coupon 108, including carriers 74 and associated slugs 134 and 135, is bonded to the wafer 140 so the parylene-C coating 136 of coupon 108 is bonded to the parylene-C layer 144 of wafer 140. This bonding process is performed by wafer level parylene-to-parylene bonding or microwave bonding. As a consequence of this bonding process, the wings 133 of the individual carriers 74 flatten out so as return to the plane of coupon 108, FIG. 7. FIG. 7, and subsequent FIGS. 8-12, are lateral cross sectional views across a single carrier and the surrounding sections of the coupon 108 adjacent the carrier. The two outer most slots represent the gap between the electrode array assembly under fabrication and the adjacent section of the coupon 108. The four slots between the outermost slots are void spaces that eventually become portions of the tab-defining slots 52.

In FIG. 7, dashed line 143 represents the separation between the parylene-C coating 136 of the carrier 74 and the parylene-C layer of 144 of the silicon wafer 108. These two layers 136 and 144 of parylene-C are eventually become the lower insulating layer 72 of the electrode array assembly 40. Accordingly, in subsequent FIGS. 8-15, these layers of a common material, the parylene-C, are shown as a single layer and are identified as insulating layer 72.

As a consequence of the bonding of coupon 108 and the carriers 74 formed thereon to the silicon wafer 140, the wafer functions as a substrate. This substrate supports both the carriers 74 and the subsequent materials bonded to the carrier during the remainder of the electrode array assembly fabrication process.

Figure 8:
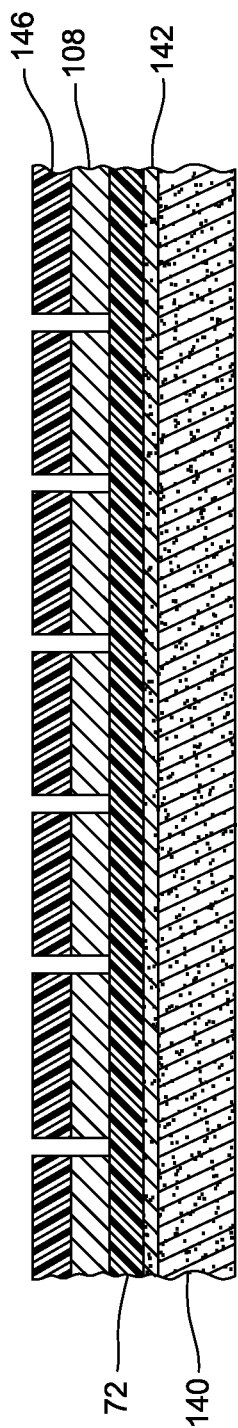
FIG. 8 is a cross sectional view of the section of the sheet of superelastic material with a layer of parylene over the formally exposed surface of the sheet.

Fabrication of electrode array assemblies 40 continues with the deposition of a parylene-C layer 146 over the exposed upper surface of coupon 108 and carriers 74, illustrated by FIG. 8. Parylene-C layer 146 has a thickness of at least 1 micron and is deposited over the coupon 108, including carriers 74 using a vapor deposition process. While not illustrated, is should be understood that the parylene-C forming layer 146 also coats the side surfaces of the carriers 74 around slots 120, 124, 126 and 128.

Figure 9:
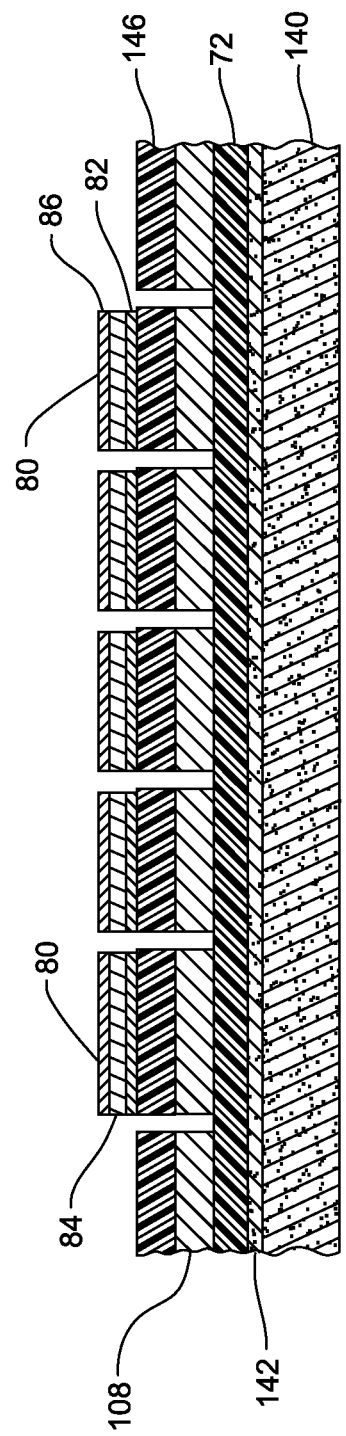
FIGS. 9, 10, 11 and 12 are cross sectional views of the section of the sheet of superelastic material showing the fabrication of the components forming the electrode array assembly on one of the carriers of the sheet.
Figure 10:
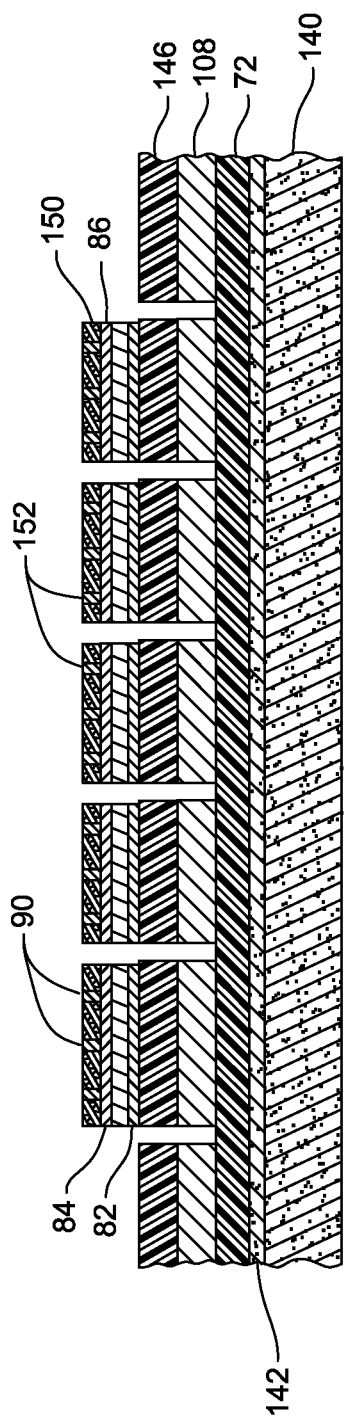
Figure 11:
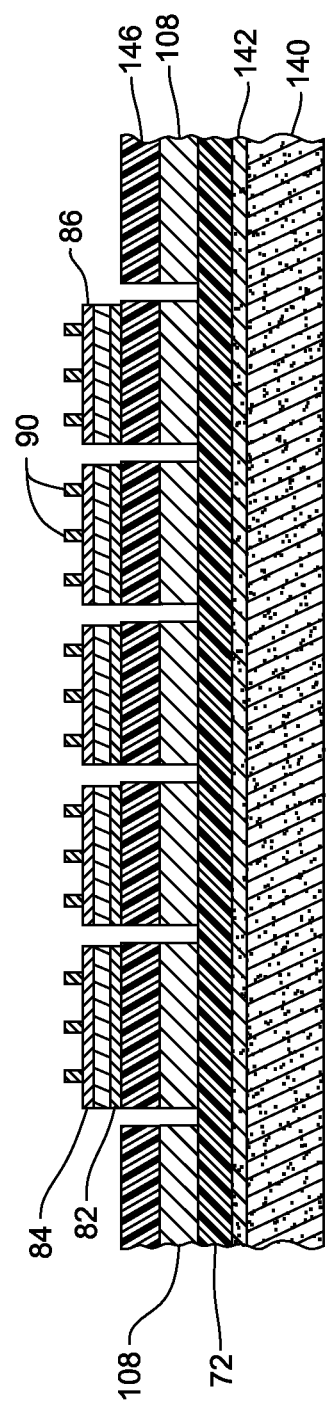
Figure 19A:
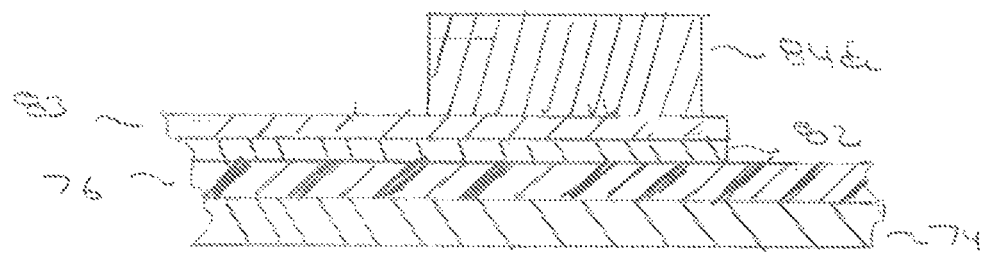
FIGS. 19A and 19B are cross sectional views illustrating how the electrode and conductor intermediate layers can are fabricated so as to have different thicknesses.
Figure 19B:
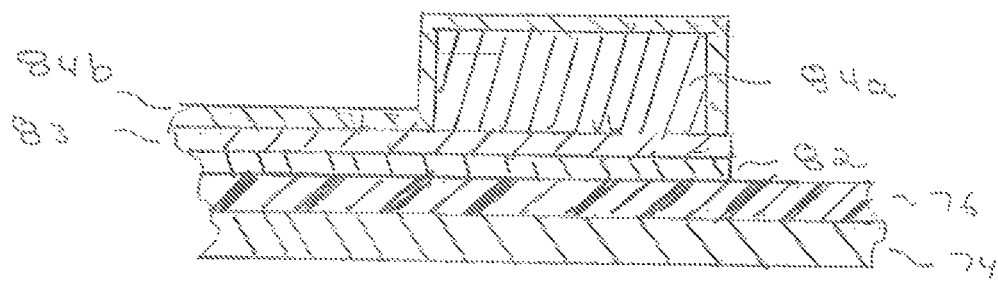

Once layer 146 is formed over the carriers 74, semiconductor and microcomponent fabrication processes are then employed to fabricate the electrodes 50, the conductors 62 and shell over the carriers 74a. Each step of the process is conducted simultaneously on each carrier 74 integral with coupon 108. In brief, layers of chrome and gold are applied over and selectively removed from the carriers to form the conductors 62 and electrode base pads 80 as seen in FIG. 9. The incorporated-by-reference U.S. Provisional Pat. App. No. 61/034,367 and PCT Pat. App. No. PCT/US2009/033769 provide more detailed explanations of the process steps by which these components of the electrode array assembly 40 are formed. Thus, it should be understood that after the chrome of the bottom layer 82 is applied, a small seed layer of gold, layer 83, seen only in FIGS. 19A and 19B, is applied prior to the step of plating intermediate layer 84.

Fabrication of the one or more electrode array assemblies 40 continues with the fabrication of the iridium buttons 90 over the electrode base pads 80. This process begins with the formation of a mask 150 over each partially fabricated assembly, FIG. 10. Mask 150 has a thickness greater than that of the conductive buttons 90. While mask 150 covers most of each assembly, there are openings 152 over the surfaces of the electrode base pad chrome top layers 86 where the buttons are to be formed.

Once mask 150 is formed, iridium is sputtered over the one or more partially fabricated assemblies 40. A fraction of this iridium enters the mask openings 152 to define the conductive buttons 90. Not shown is the iridium that is deposited over the mask. Once the iridium is deposited, mask 150 is removed. The removal of masks 150 leaves only buttons 90 extend above the chrome top layers 90 of the electrode base pads 90, FIG. 11. For ease of illustration in FIGS. 10-12, only three buttons 90 are shown with each electrode. In practice, each row of buttons typically contains appreciably more buttons 90.

During the above fabrication steps of this invention, iridium is not deposited on the top layers of the conductors 62.

Figure 12:
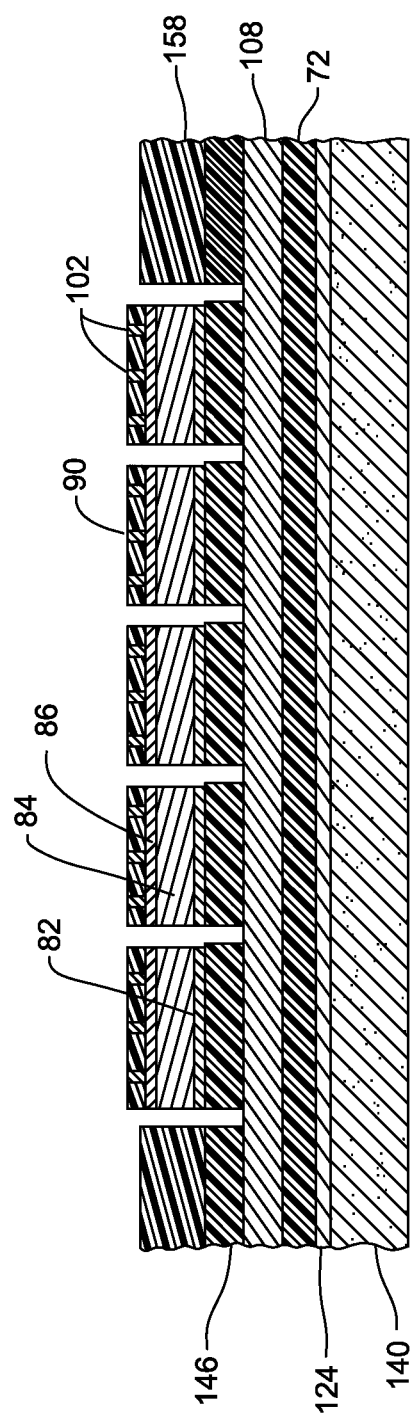

Once electrode buttons 90 are formed, a layer 158 of parylene-C that becomes shell 98 is deposited over the whole of the partially fabricated assembly, FIG. 12. More particularly, the parylene-C layer 158 is deposited over the exposed surfaces of parylene-C layer 146 and the conductors 68. The parylene-C of layer 158 has a thickness slightly greater than that of the conductive buttons 90 Accordingly, while not illustrated, it should be understood that the parylene-C of layer 158 is initially applied to completely cover the conductive buttons 90. Once layer 158 is applied, openings 102 are formed in the layer to expose the outer faces of the conductive buttons 90. More particularly, the parylene-C of layer 158 is removed so that, post removal, at least a portion of the parylene-C, as seen in FIG. 2, extends around the outer parameters of the faces of the conductive buttons 90. Thus, layer 158 becomes the outer shell 98. Accordingly, in FIGS. 13-15 this layer of parylene is relabeled as shell 98 in FIGS. 13-15.

Shell 98 thus does more than function as the non-conductive outer shell of the electrode assembly 40. In the process of removing parylene-C layer 158 to form the shell, openings 102 are formed so as to not wholly expose the faces of the underlying buttons. Instead, openings 102 have a diameter less than that of the conductive buttons. Consequently, as mentioned above, shell 98 projects over the outer perimeter of the buttons 90. Shell 98 thus also holds the conductive buttons 90 to the electrode base pads 80 with which the buttons are associated.

The formation of shell 98 completes the component-addition processes of the fabrication of electrode array assembly 40. Assembly 40, more particularly, the assembly carrier 74, is then removed from the coupon 108 and the underlying silicon wafer 140.

The removal process starts with the removal of the parylene-C from over the retaining tabs 122 and 127, step not shown. Consequently, above each opening 120 there is a parylene-C free void space. This void space, represented by identification number 162 in FIG. 13 is shown above one of the retaining tabs 122 that extend across each opening. In FIG. 13, the retaining tab 122 is the section of the superelastic material between the two dashed lines. The assembly to the left of the tab 122 is the essentially fabricated electrode array assembly 40. The assembly to the right of the tab includes the portion of the coupon 108 and surrounding parylene-C that is left behind after the lift off process. Since FIGS. 13-15 only represent the section of the assembly adjacent the end of the foot 46, not seen in these Figures are the layers of material forming the electrodes or conductors. The cross sectional view of a retaining tab 127 and the associated slug 134 or 135 is essentially identical to that of the depiction of tab 122 in FIG. 13. Accordingly, as the removal processes are identical, the removal of the tabs 127 is not illustrated. Below each retaining tab 122 and 127 a section of parylene-C is present as a result of the bonding of the parylene-C layers 136 and 144 forming lower insulating layer 72.

The coupon and carrier forming superelastic forming tabs 122 and 127 is removed by a chemical etching process or a mechanical process. Once tabs 122 and 127 are removed, the parylene below where the tabs were present is removed. As a consequence of these processes, the assembly appears as in FIG. 14. Opening 162, which is part of a slot 120 of FIGS. 4A and 4B now forms a continuous separation between the electrode array assembly and the surrounding section of the parylene-coated coupon 108. While not shown, it should be appreciated that as a result of these material removal processes, each of slots 126 and 128 also is transformed into a closed loop slot. As a consequence of the closing of each of the slots 126 and 128 slugs 134 and 135 are separated from the fabricated electrode array 40 assembly that surrounds the slugs. In addition to the slugs 134 and 135 of superelastic material separating from the associated electrode array assembly in these processes, the material deposited above each slug is also separated from the assembly 40. At this stage of the process, the electrode array assembly 40 and the material laden slugs within the assembly are still bonded to the silicon wafer 140.

Final separation of the assembly 40 from the workpiece is performed by removal of sacrificial layer 142. This removal process is not selective so that removal of layer 142 also results in the separation of coupon 108 from wafer 140 as seen in FIG. 15. As a consequence of the removal of sacrificial layer 142, the electrode array assembly 40 is wholly separated from both coupon 108 and wafer 140. Assembly 40 is then lifted off from the wafer 140 and away from sheet. Since the material-coated slugs 134 and 135 were previously separated from the assembly 40, the slugs are left behind on the wafer to define the void spaces between the assembly legs 44 and center opening 64 of assembly foot 46.

As a consequence of the electrode array assembly 40 being lifted off wafer 140, the assembly head 42 develops the curved profile of carrier head 112 as represented by FIG. 1A. This curvature is not seen in FIG. 15 because the cross sectional view this Figure is a longitudinal slice view; the curvature is along the lateral axis of the assembly 40. The electrodes 48 and conductors 60 are disposed on the inwardly curved face of the assembly 40.

Once electrode array assembly 40 is lifted off wafer 140, the assembly is ready for further processing the specifics of which are not relevant to this invention. This further processing can involve folding the electrode array assembly along a number of fold lines parallel to the longitudinal axis of the assembly. The folded assembly is then placed into a delivery cannula. When the assembly is deployed from the delivery cannula against a section of tissue, owing to carrier 74 being formed from super-elastic material, the assembly unfolds to the curved shape. This facilitates surface contact between the conductive buttons 90 of the electrodes 48 and the underlying tissue.

An advantage of assembling electrode array assembly 40 according to the method of this invention is that the conductive elements of the assembly are formed directly on the superelastic carrier 74. This eliminates the process steps associated with bonding a first subassembly that includes the electrodes and conductors to a second subassembly that includes the super elastic carrier.

Another feature of this invention is that silicon wafer 140 functions as a structural backing, a substrate, for the assembly 40 while the assembly is being fabricated. The silicon wafer 140, owing to its mechanical strength, withstands the pressures of the process steps associated with the fabrication of the various components of the assembly on the carrier 74. Since the wafer 140 absorbs these stresses without bending or breaking, the need to provide the carrier with sufficient strength so it can withstand these stresses is eliminated. Avoiding having to provide a carrier that can withstand these stresses likewise avoids the increased carrier thickness reduced carrier elasticity that results from having to design the carrier to resist these forces.

Another benefit of the method of this invention is that plural carriers 74 can be formed on a single coupon 108 of super elastic material. While the carriers 74 remain attached to the coupon 108, the remaining components forming each electrode array assembly 40 can be fabricated over the individual carriers. Thus, the method of this invention, in addition to simplifying the process steps associated with the assembly of a single electrode array assembly 40, also makes it possible to batch fabricate plural assemblies 40.

III. Alternative Versions

It should be appreciated that the foregoing is direct to one specific method of assembly of this invention. Alternative versions of the invention are possible.

Figure 16A:
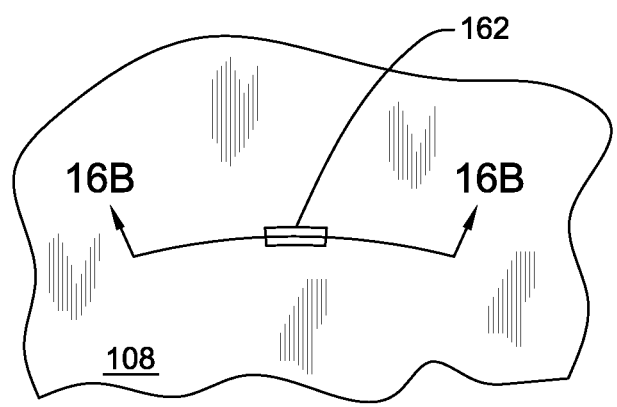
FIGS. 16A and 16B are, respectively, plan and cross sectional views of a portion of the coupon illustrating an initial step in the formation of the coupon-to-carrier tabs and the carrier-to-slug tabs formed on the coupon.
Figure 16B:
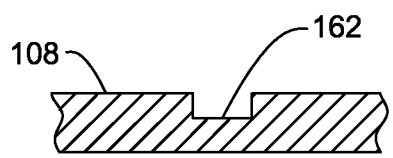

Other methods of this invention may have less than, more than or different process steps than what has been disclosed. For example, in some versions of the invention, the formation of the carriers 74 starts with the formation of the tabs that hold the carriers to the coupons and that hold the slugs 134 and 135 to the carriers. This is seen in FIGS. 16A and 16B. As illustrated in these Figures, the portions of the coupon 108 are partially etched (not completely etched through) to define notches 172 (one shown). Each notch 172 has a depth that is between 25 and 75% of the total thickness of the coupon 108. Often, the notches 172 have a depth between 40 and 60% of the total thickness of the coupon 108. Notches 172 are formed in the coupon over the sections of the coupon that become the tabs.

Figure 17A:
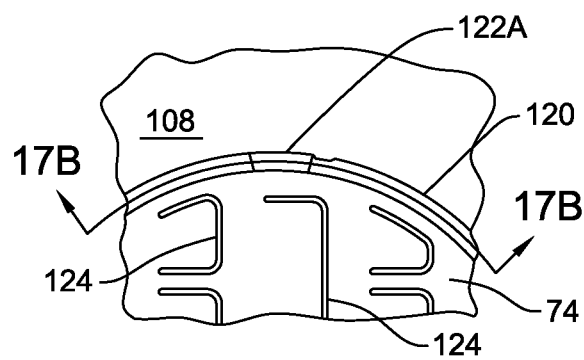
FIGS. 17A and 17B are, respectively, plan and cross sectional views of a portion of the coupon illustrating one of the coupon-to-carrier tabs after the formation of the carrier from a section of the coupon.
Figure 17B:
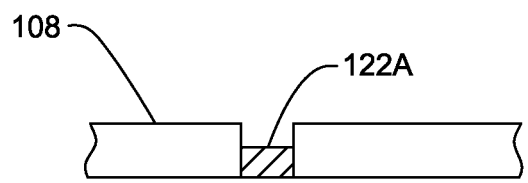

Once notches 172 are formed, coupon 108 is shaped to form the slots 120, 124, 126 and 128 that define the inner and outer perimeters of each carrier 74. This etching removes material through the whole of the thickness of the coupon 108. This etching step is specifically not performed on the sections of the coupon 108 that define the bases of the notches 172. Consequently, the coupon 108 develops the shape as depicted in FIGS. 17A and 17B. In FIG. 17A the sections of a slot 120 that defines the carrier head is shown. For ease of illustration, only a few of the slots 124 in this portion of the head are shown. As seen in FIG. 17B, as a consequence of these two carrier material removal etches, coupon-to-carrier tabs and carrier-to-slug tabs are defined, a single coupon-to-carrier tab 122A being illustrated. Given the previous formation of notches 172 each, these tabs have a thickness between 25 to 75% of the thickness of the coupon 108. Each of these tabs has a face that is coplanar with one of the faces of the coupon 108. If the carriers are plastically deformed, bent, the tabs are located so the tab faces coplanar with the coupon 108 are coplanar with the coupon face that is concave face with regard to the bend of the carrier away from the coupon. With respect to FIG. 5A, this mean that the tabs have faces that are coplanar with the faces of the carrier 74 and coupon 108 opposite the face seen in this Figure.

Figure 18:
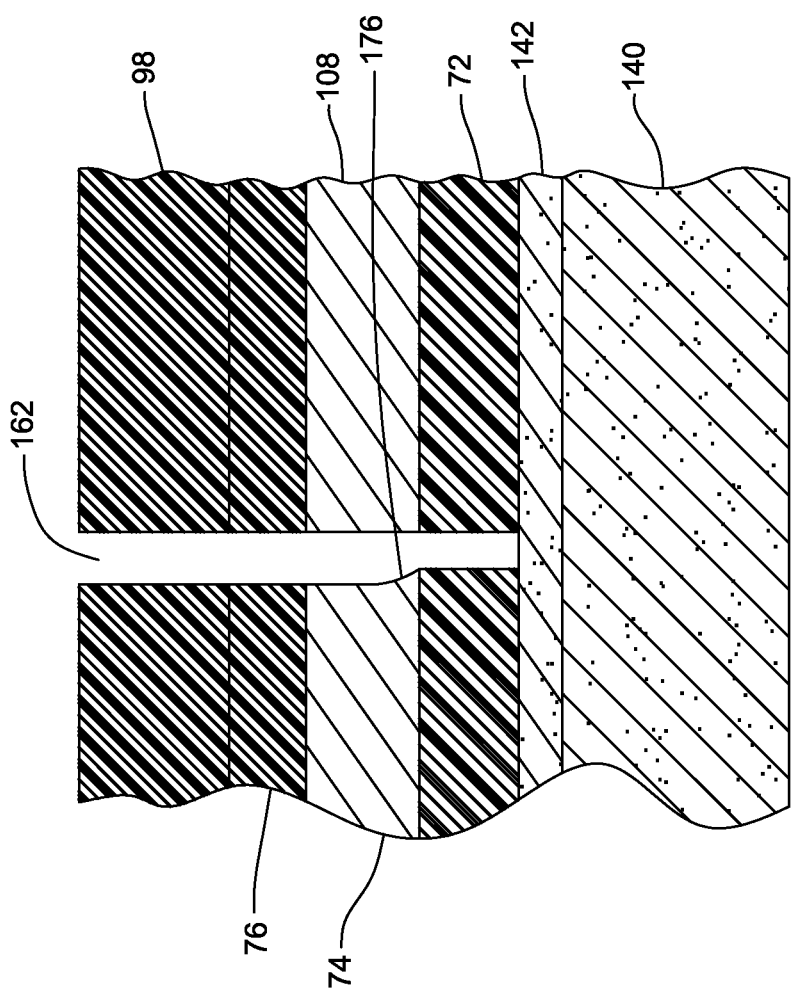
FIG. 18 is a cross sectional view illustrating the perimeter of the electrode array assembly of this invention after the layers of insulating material and the tab are separated from the surrounding coupon.

An advantage of employing reduced thickness tabs to hold the carriers 74 to coupons 108 and the slugs 134 and 135 to the carriers 74 is seen by reference to FIG. 18. Here, the results of the etching process used to removing a tab 122A from the coupon 108 are shown. In most etching processes, the removal, the etching away of the material forming the tab is not simply along a line perpendicular to the mask opening through which the etchant is applied. Instead, the etching forms a boundary surface of this material that flares inward from the perimeter of the mask opening. As a consequence of the boundary forming along this non-linear path, the remaining material forms an outwardly projecting crest 176. In the method of the invention, the thickness of the tabs that need to be removed is less than the thickness of the coupon 108. Consequently, both the extent the distance to which the crest 176 extends outwardly and the acuteness of the angle of the crest are reduced relative to that of a crest formed as a result of the etching away a tab having a thickness equal to that of the coupon 108. The minimization of both the extent the crest 176 extends beyond the rest of the assembly 40 and the angle of this crest reduces the likelihood that, when the assembly is implanted, the crest inadvertently injures adjacent tissue.

Likewise, in some versions of the invention, two or more layers of the insulating material and conductive material used to form the electrodes and conductors of each array 40 may initially formed as a subassembly that is not on the coupon 108. Once this subassembly is formed, it is bonded to the coupon 108.

There is no requirement that, in all versions of the invention, all described process steps be executed or that the process steps be executed in the order described. For example, in some methods of this invention, prior to the formation of the one or more carriers on the coupon, the materials forming the array electrodes and conductors are bonded to sections of the coupon 108 that later become the one or more carriers 74. Once these materials are applied to the coupon, the sections of the coupons over which these materials are applied are first severed from and then removed from the remainder of the coupon. Each of these removed sections of the coupon 108 becomes a carrier 74 for one of the electrode arrays 40. Alternatively, after some of the layers of the material forming the array electrodes 48, conductors 62 and insulating layers may first be disposed on one or more sections of the coupon 108, the coupon is then shaped to form the one or more carriers 74. After these process steps are completed, additional materials are disposed on the carriers 74 to complete the process of forming the individual electrode arrays 40.

Also, depending on the materials from which the electrode arrays 40 are formed, the final step in the removal of the assembly from the workpiece to which the assembly is held during the fabrication may be the removal of the retaining tabs that hold the assembly to the sheet of plastically deformable material.

Alternatively, depending on the nature of the plastically deformable material, once the electrode assembly is fabricated, the whole of the surrounding sections of plastically deformable material are removed from the support substrate. Once this step is performed, the sacrificial layer is removed. An advantage of this version of the invention is that it reduces the extent to which a precise lift off process is required to remove the electrode array assembly from the support substrate.

Similarly, there is no requirement that in all versions of the invention, the carrier 74 be curved or that the carrier be formed from a plastically deformable material. In alternative applications of this invention, it may be desirable to fabricate the electrode array assembly on a carrier that has a high degree of flexibility and resists tearing, for example a polyamide film. This is so the assembly could be disposed over tissue that has a relatively bumpy or irregular surface pattern. Using the method of this invention, the carrier can be bonded to the support wafer or other rigid substrate prior to the formation of the conductive components on top of the carrier. Once the assembly is fabricated, the assembly is removed from the support wafer. In these versions of the method of the invention, the only component attached to the substrate is the flexible carrier without any surrounding coupon.

Likewise, materials other than the described materials can function as the base materials from which the components of each electrode array assembly 40 are fabricated. Thus, the carrier 74 may be formed out of a superelastic material other than a nickel titanium alloy. Again, some versions of the invention, this material may need only be material that can be flexible or plastically deformed and not superelastic. In some versions of the invention, the material from which the carrier may be formed may be non-conductive. If such a material is employed as the carrier, it could eliminate the need to provide a layer of non-conductive material between the carrier and the conductive components. Thus, it should be understood, less or more layers of material that what has been described with respect to the exemplary version of the invention may be needed to fabricate an electrode array assembly 40 in other versions of this invention. Materials other than chrome may be used as adhesion layers around the gold layers. For example, in some versions of the invention the adhesion layer may be formed from titanium.

Likewise, the actual process steps used to apply the material that forms the layers of insulating and conductive materials on the carriers 74 may vary with the nature of the materials. In some versions of the invention, it may be desirable to prepare the surface of the carrier to ensure and/or improve the adhesion of insulating material to the carrier. For example, it may be desirable to deposit an oxide layer on the surface of a Nitinol carrier/coupon to ensure the adhesion of the parylene to this structure.

In some versions of the invention, each electrode conductive button may include a pedestal formed from a first material and a head, that forms the exposed face of the button, formed from a second material. Thus, in some versions of the invention, the pedestal is formed from titanium. The head can be formed from iridium. Alternatively, in some versions of the invention, instead of having individual conductive buttons, each electrode may have a sheet of material the exposed face of which functions as the interface surface across which current is flowed to/from the adjacent tissue. This sheet can, for example be a layer of iridium, iridium oxide, platinum or platinum oxide. In some embodiments of this version of the invention, the shell is formed with openings through which individual sections of this sheet are exposed. Alternatively, in some embodiments of this version of this invention, substantially 30% or more or even 50% or more of the whole of this material is exposed as a continuous surface to form the exposed face of the electrode. Again, it may be appropriate to have a layer of intermediate material between the conductive base of the electrode and the material forming the exposed head of the electrode.

In some versions of this invention, the conductive buttons are formed by a combination of these processes. Specifically, conductive posts formed from the one, two or even more layers of material are formed on base pads of the electrodes. These posts may have cross sectional shapes that are circular or polygonal in shape. Insulating material is disposed over these posts. Portions of the exposed faces of these posts are exposed to form the conductive surfaces of the electrode. The area of each of these exposed faces, conductive surfaces, is typically less than the cross sectional area of the post with which the face is integral.

It should likewise be appreciated that this invention is not directed to electrode array assemblies having the above-described shape. For example, it may not be necessary to form the assembly and underlying carrier 74 with spaced-apart legs that extend from the section on which the electrodes are formed. Similarly, it may not be necessary to provide an opening in the assembly or carrier for receiving the cable that includes the current-supplying conductors that are connected to the individual electrodes. Likewise in not all versions of the invention are the electrodes formed on tabs that are separate from the surrounding sections of the carrier.

Similarly, there is no requirement that, in all versions of the invention, a silicon wafer serve as the support substrate. In some versions of the invention a rigid polymer or other plastic may serve this function. In this version and other versions of the invention, an adhesive may be used to releasably bond the insulating layer to the support substrate. Then once the electrode array assembly/assemblies is/are fabricated, the adhesive bond is broken either chemically or mechanically to remove the assembly/assemblies from the support substrate.

Also, it should be appreciated that, unless specifically set forth in the claims, the dimensions of the various components and material layers are for purposes of example only and are not limiting. Thus, in some versions of the invention, the gold intermediate layer 84 of the electrode bond pad may have a thickness of 10 microns or more and some versions of the invention a thickness of 20 microns or more. A reason it may be desirable to proved the electrodes with relatively thick intermediate layers is to increase the radiopacity of the assembly 40

In these and other versions of the invention, the thickness of the gold intermediate layers of the conductors 62 is less than that of the electrodes 48. One process for fabricating an electrode array having these characteristics is described by initial reference to FIG. 19A. This Figure represents that, in a first plating process, spaced apart layers of gold, layers 84a, (one shown) are applied to the assembly under formation. In FIG. 19A, the layer 84a is shown deposited above the thin gold seed layer 83 that is disposed above the bottom (adhesion) layer 82. In this step, the layers 84a are applied so as to not extend over the outer perimeters of the seed layers 83 that define the outer perimeters of the electrodes 48. Instead, layers 84a are applied so as to have an outer surface that is recessed approximately 25 microns inwardly from outer edges of the adjacent portions of the seed layers 83. In this plating step, layers 84a are applied to have a thickness equal to the difference between the desired thickness of the intermediate layers for the electrodes 48 and the thickness of the intermediate layers of the conductors 62.

In a second plating step, represented by FIG. 19B, gold is applied over the seed layers 83 to form the intermediate layers 84b of the conductors 62. In this plating step, the gold forming layers 84b is applied to further cover the outer surfaces of electrode intermediate layers 84a (single layer 84b shown). Often the gold forming the layers 84b is formed to have thickness of approximately 2 microns. The deposit of the second gold of the layers 84b over the previously formed gold of layers 84a of the electrodes effectively welds the two gold layers together. The gold forming the intermediate layers, the combination of layers 84a and 84b, can be considered welded to the gold of the conductors 62, the layers 84b. In this process, the gold of layer 84b is applied so that it covers the exposed portions of the seed layers 83 that are between the outer edges of the seed layer and the adjacent surfaces of the gold layers 84a.

At the completion of the above process steps, the gold-on-gold layers 84a and 84b can be considered to be the thick intermediate conductive layers of the electrodes 48. The gold layers 84b are the thin intermediate conductive layers of the conductors 62.

Likewise, it should be understood electrode array assemblies can be fabricated according to this invention that include just a single column of electrodes. This type of assembly may have a nerve cuff. It should therefore be appreciated that to fit around a nerve, this assembly may have a width as small as 0.25 mm. This invention can also be used to form an implantable electrode array assembly that has a single electrode 48 with a single complementary conductor 62.

Alternatively, instead of forming the assembly of this invention so it curves around an axis parallel to the longitudinal axis of the assembly, the curvature is around an axis parallel to the lateral axis. Still in some versions of the invention, the axis of curvature may be off angle to both the longitudinal and lateral axes of the assembly. Likewise, in some versions of the invention, depending of the application of the electrode array assembly, the carrier may be formed to have plural sections with different curvatures.

Therefore, it is an object of the appended claims to cover all such variations and modifications that come within the true spirit and scope of this invention.

What is claimed is:

1. A method of assembling an implantable electrode array, the method including the steps of:
   providing a coupon that lies in a plane and is formed of a flexible material;
   at least partially shaping carrier-defining sections of the coupon such that carriers extend out the plane of the coupon;
   bonding the coupon including the carriers to a rigid substrate;
   while the carriers are bonded to the rigid substrate, applying at least one layer of insulating material and at least one layer of conductive material in separate steps to an exposed face of the carriers to form at least one electrode and at least conductor on each of the carriers; and
   after formation of the at least one electrode and the at least one conductor on the carriers, releasing the carriers from the rigid substrate so that each carrier and the at least one electrode and the at least one conductor formed thereon form an electrode array assembly, and further separating the carriers from an adjacent section of the coupon.

2. The method of assembling an implantable electrode array of claim 1, further comprising forming the coupon of plastically deformable material.

3. The method of assembling an implantable electrode array of claim 1, further comprising forming the coupon of polyamide film.

4. The method of assembling an implantable electrode array of claim 1, wherein separating the carriers from the adjacent section of the coupon occurs prior to releasing the carriers from the rigid substrate.

5. The method of assembling an implantable electrode array of claim 1, further comprising at least partially shaping the coupon to define the carriers.

6. The method of assembling an implantable electrode array of claim 5, wherein:
   at least partially shaping the coupon to define the carriers comprises forming slots in the coupon to define the carriers and forming at least one tab that intersects the slots to connect the carriers to the adjacent section of the coupon; and
   after applying the at least one layer of insulating material and the at least one layer of conductive material to the coupon, and as part of separating the carriers from the adjacent section of the coupon, removing the at least one tab connecting each carrier to the coupon.

7. The method of assembling an implantable electrode array of claim 1, wherein:
   prior to applying the at least one layer of insulating material and the at least one layer of conductive material to the coupon, mounting the coupon to the rigid substrate; and
   during applying the at least one layer of insulating material and the at least one layer of conductive material to the coupon, further applying the at least one layer of insulating material and conductive material to the exposed face of the carriers; and
   after applying the at least one layer of insulating material and the at least one layer of conductive material to the coupon, releasing the coupon from the rigid substrate.

8. A method of assembling an implantable electrode array, the method including the steps of:
   bonding a carrier formed of a superelastic material to a rigid substrate;
   while the carrier is bonded to the rigid substrate, applying at least one layer of insulating material and at least one layer of conductive material in separate steps to an exposed face of the carrier to form at least one electrode and at least conductor on the carrier; and
   after formation of the at least one electrode and the at least one conductor on the carrier, releasing the carrier from the rigid substrate so that the carrier and the at least one electrode and at least one conductor formed thereon form an electrode array assembly.

9. The method of assembling an implantable electrode array of claim 8, wherein:
the carrier is part of a coupon that is larger in size than the carrier;
in the step of bonding the carrier to the rigid substrate, the coupon is bonded to the rigid substrate;
in the step of applying the at least one layer of insulating material and the at least one layer of conductive material to the carrier, the at least one layer of insulating material and conductive material is applied to plural sections of the coupon with each section being in one of a plurality of carrier-defining sections of the coupon; and
the method further includes separating the carrier-defining sections of the coupon from an adjacent section of the coupon.

10. The method of assembling an implantable electrode array of claim 8, wherein the superelastic material comprises nickel titanium alloy.

11. The method of assembling an implantable electrode array of claim 8, further comprising partially shaping the carrier so that the carrier has a non-planar shape, wherein bonding the carrier to the rigid substrate further comprises causing the carrier to flex into a planar shape as a result of the bonding, and wherein releasing the carrier from the rigid substrate further comprises causing the carrier to at least partially return to the non-planar shape the carrier had prior to the step of bonding the carrier to the rigid substrate.

12. The method of assembling an implantable electrode array of claim 8, further comprising partially shaping the carrier to have at least one tab that is partially separated from adjacent portions of the carrier, wherein during the step of applying the at least one layer of insulating material and the at least one layer of conductive material to the carrier, the at least one layer of conductive material is applied to the carrier to form an electrode on the at least one tab.

13. A method of assembling an implantable electrode array, the method including the steps of:
partially shaping a carrier formed of flexible material so that the carrier has a non-planar shape;
bonding the carrier to a rigid substrate that is planar and causing the carrier to flex into a planar shape as a result of the bonding;
while the carrier is bonded to the rigid substrate, applying at least one layer of insulating material and at least one layer of conductive material in separate steps to an exposed face of the carrier to form at least one electrode and at least conductor on the carrier; and
after formation of the at least one electrode and the at least one conductor on the carrier, releasing the carrier from the rigid substrate so that the carrier and the at least one electrode and at least one conductor formed thereon form an electrode array assembly.

14. The method of assembling an implantable electrode array of claim 13, wherein:
the carrier is part of a coupon that is larger in size than the carrier;
in the step of bonding the carrier to the rigid substrate, the coupon is bonded to the rigid substrate;
in the step of applying the at least one layer of insulating material and the at least one layer of conductive material to the carrier, the at least one layer of insulating material and conductive material is applied to plural sections of the coupon with each section being in one of a plurality of carrier-defining sections of the coupon; and
the method further includes separating the carrier-defining sections of the coupon from an adjacent section of the coupon.

15. The method of assembling an implantable electrode array of claim 13, further comprising forming the carrier of one of the following:
plastically deformable material;
superelastic material; or
polyamide film.

16. The method of assembling an implantable electrode array of claim 13, further comprising partially shaping the carrier to have at least one tab that is partially separated from adjacent portions of the carrier, wherein during the step of applying the at least one layer of insulating material and the at least one layer of conductive material to the carrier, the at least one layer of conductive material is applied to the carrier to form an electrode on the at least one tab.

17. The method of assembling an implantable electrode array of claim 13, wherein releasing the carrier from the rigid substrate further comprises causing the carrier to at least partially return to the non-planar shape the carrier had prior to the step of bonding the carrier to the rigid substrate.

18. A method of assembling an implantable electrode array, the method including the steps of:
partially shaping a carrier formed of flexible material to have at least one tab that is partially separated from adjacent portions of the carrier;
bonding the carrier to a rigid substrate;
while the carrier is bonded to the rigid substrate, applying at least one layer of insulating material and at least one layer of conductive material in separate steps to an exposed face of the carrier to form at least one electrode and at least conductor on the carrier, wherein applying the at least one layer of conductive material forms the at least one electrode on the at least one tab; and
after formation of the at least one electrode and the at least one conductor on the carrier, releasing the carrier from the rigid substrate so that the carrier and the at least one electrode and at least one conductor formed thereon form an electrode array assembly.

19. The method of assembling an implantable electrode array of claim 18, wherein:
the carrier is part of a coupon that is larger in size than the carrier;
in the step of bonding the carrier to the rigid substrate, the coupon is bonded to the rigid substrate;
in the step of applying the at least one layer of insulating material and the at least one layer of conductive material to the carrier, the at least one layer of insulating material and conductive material is applied to plural sections of the coupon with each section being in one of a plurality of carrier-defining sections of the coupon; and
the method further includes separating the carrier-defining sections of the coupon from an adjacent section of the coupon.

20. The method of assembling an implantable electrode array of claim 18, further comprising forming the carrier of one of the following:
plastically deformable material;
superelastic material; or
polyamide film.

21. The method of assembling an implantable electrode array of claim 18, further comprising partially shaping the carrier so that the carrier has a non-planar shape, wherein bonding the carrier to the rigid substrate further comprises causing the carrier to flex into a planar shape as a result of the bonding, and wherein releasing the carrier from the rigid substrate further comprises causing the carrier to at least partially return to the non-planar shape the carrier had prior to the step of bonding the carrier to the rigid substrate.

22. A method of assembling an implantable electrode array, the method including the steps of:
- bonding a carrier formed of flexible material to a rigid substrate, the carrier being part of a coupon that is larger in size than the carrier and further comprising bonding the coupon to the rigid substrate;
- at least partially shaping the coupon to define the carrier by forming slots in the coupon to define the carrier and by forming at least one tab that intersects the slots to connect the carrier to an adjacent section of the coupon;
- while the carrier is bonded to the rigid substrate, applying at least one layer of insulating material and at least one layer of conductive material in separate steps to an exposed face of the carrier to form at least one electrode and at least conductor on the carrier, and further applying the at least one layer of insulating material and conductive material to plural sections of the coupon with each section being in one of a plurality of carrier-defining sections of the coupon; and
- after formation of the at least one electrode and the at least one conductor on the carrier, releasing the carrier from the rigid substrate so that the carrier and the at least one electrode and at least one conductor formed thereon form an electrode array assembly, and further separating the carrier-defining sections of the coupon from the adjacent section of the coupon, and as part of separating the carrier-defining sections, further removing the at least one tab connecting the carrier to the adjacent section of the coupon.

\* \* \* \* \*